United States Patent [19]

Hosemann et al.

[11] Patent Number: 4,688,240
[45] Date of Patent: Aug. 18, 1987

[54] NON-DESTRUCTIVE TESTING OF FIBER REINFORCED STRUCTURAL MATERIALS

[75] Inventors: Rolf Hosemann, Berlin; Walter Mayland, Stuhr; Juergen Walter, Ganderkesee, all of Fed. Rep. of Germany

[73] Assignee: Erno Raumfahrttechnik GmbH, Bremen, Fed. Rep. of Germany

[21] Appl. No.: 669,316

[22] Filed: Nov. 7, 1984

[30] Foreign Application Priority Data

Nov. 11, 1983 [DE] Fed. Rep. of Germany ....... 3340790
Jul. 3, 1984 [DE] Fed. Rep. of Germany ....... 3424384

[51] Int. Cl.⁴ ..................... G01T 1/36; G01N 23/201; G01N 23/20
[52] U.S. Cl. ....................................... 378/70; 378/83; 378/88
[58] Field of Search ................................. 378/70-73, 378/75-78, 79, 80, 81, 82, 83, 88, 89, 90

[56] References Cited

PUBLICATIONS

Klug et al., *X-Ray Diffraction Procedures for Polycrystalline and Amorphous Materials,* John Wiley & Sons, Inc., 1954, pp. 554-568, 621-626.

*Primary Examiner*—Janice A. Howell
*Assistant Examiner*—Charles F. Weiland
*Attorney, Agent, or Firm*—Ralf H. Siegemund

[57] ABSTRACT

Different reflection patterns of monochromatic x-rays are used to determine quality defining parameters of fiber reinforced compounds.

15 Claims, 6 Drawing Figures

NON-DESTRUCTIVE TESTING OF FIBER REINFORCED STRUCTURAL MATERIALS

BACKGROUND OF THE INVENTION

The present invention relates to a method for non-destructive testing of structural material, including particularly fiber reinforced compound products and using x-ray testing and detector imaging.

Non-destructive methods for testing of fiber reinforced structural materials, including particularly compound elements under utilization of x-rays is basically a known procedure. Such a method usually ascertains the so-called coarse structure or texture of the compound system. On the other hand, x-rays are known to be amenable towards the detection of density differences in test objects generally so that there is no reason that compound parts should not be tested towards irregularities in terms of density differences.

However, compound components with fiber reinforcement has the particular property in that the density of fibers on one hand, and the density of the resin binder (host material) on the other hand, are quite similar so that similar overall density may be represented by a high as well as by a low content of fibers. Therefore, x-ray testing of such parts under consideration of coarse texture aspects will not yield significant and adequately unambiguous density distributions in terms of fiber versus binder. For example, local bunching and local depletion of fibers hardly show up in such a test. Therefore, such a texture investigation will not be sufficiently accurate concerning the integrity of the tested part.

DESCRIPTION OF THE INVENTION

It is an object of the present invention to provide a new and improved x-ray test method for non-destructive testing of fiber reinforced compound parts permitting unambiguous measuring results with regard to density distribution in terms of relative fiber content.

It is therefore a specific object of the present invention to provide a new and improved method of non-destructive testing of fiber reinforced compound parts using x-rays and detector imaging.

It is a feature of the invention to use diffraction and reflection patterns of monochromatic x-rays for distinguishing fibers from binders (host material) through the differences in crystal lattice orientations and regularities.

In accordance with the preferred embodiment of the present invention it is suggested to provide an inspection and testing of such compound objects on the basis of x-ray fine texture investigation so that any change in disposition and configuration (Gestalt) of the dispersed x-rays, the dispersal having been produced by reflection on and in polycrystalline material that is being tested, and results in particular reflection images to be used as a representation, or at least indication for local changes for instance in internal tension and stress of the test object and crystalline distribution patterns generally.

It was found that the inventive method yields unambiguous results concerning the texture of the tested structural compound fiber reinforced material. The x-ray method, particularly the fine texture investigation, does not evaluate the attenuation of x-rays as is used in so-called coarse texture investigation, i.e., the mass and material as such of the object to be tested is not investigated with regard to the resulting attenuation of the x-rays, but diffraction scattering and oriented reflections of the x-ray at the individual atoms and lattice planes in the crystalline structure is used to determine the integrity of the compound material. Thus, one uses monochromatic x-rays as they are scattered in a reflective mode in the polycrystalline material, and the orientation (direction) of the respective reflection is used as parameter and criterion concerning internal tension, stress and other texture modifications in the test object. The inventive method being based on fine texture principles uses in particular the disposition and location of individual fibers within the compound system, and uses the reflection produced by and in the fiber in order to acquire information about the orientation and locational distribution density of the fibers. One uses here in particular the paracrystalline property of fibers having long chain molecules in a highly oriented fashion, whereby particularly microparacrystals have a particular disposition with regard and in relation to the fiber axis.

The term used here "microparacrystals" in fact explicates a structural distortion wherein the outer dimensions of a crystal remain essentially invariant, but the individual vectors between adjacent unit cells may vary in size, direction and orientation under the assumption that these particular cells as such can be unambiguously defined, i.e., they must not be amorphous. From the point of view of physics, a microparacrystal constitutes a special form of a crystal whose lattice includes a large number of randomly distributed defect or imperfection points, wherein each such points produces a local microshift. Since the fibers, such as carbon fibers, as well as the surrounding resin in such a compound part, all have quite extenuated paracrystalline properties, but differ of course in the textural details, it is possible to use this property for determining by means of x-rays the fine texture of such a part.

In furtherance of practicing the invention, the detection is preferably carried out through the employment of x-ray sensitive film under utilization of certain diaphragms in order to separate particular reflections or reflective components as resulting from an interaction of the monochromatic x-ray with the compound test object. In lieu of an x-ray sensitive film, one may use positionable detectors of the electronic varieties, such as scintillation counters or the like to ascertain reflection patterns on a more detailed basis permitting in particular the immediate generation of electrical signals which are indicative of the desired measuring result. In conjunction therewith, it is, for example, advisable to provide the detection in a detection plane but in separate regions therein in which different reflections, i.e., reflections on particularly oriented lattice crystal plane, are to be expected. In conjunction therewith, one may use differently wide diaphragms so that a width difference in the detection spots parallel to the fibers provide information about the quality of the orientation within the fiber material. This involves, for example, the distribution of the size, strength and orientation of microparacrystals in the fibers, as well as of lattice defects therein. Also, it should be observed that if the fibers provide a certain orientational aspects in their microparacrystals while being embedded in a material that exhibits random distribution of molecules with or without crystalline structure, one will obtain separate detection of a so-called halo resulting from reflection of x-rays in the binder, being separately recognizable from particular reflection patterns resulting from x-ray interaction with the crystal planes in the fibers themselves.

The inventive method permits a running inspection whereby, for example, test objects and test equipment are moved continuously in relation to each other. This may involve particularly a tubular test object which should be rotated and/or axially moved to obtain, for example, a helical or a meandering pattern to continuously inspect every portion of the test object. The x-rays may in this case be generated in the interior of the tubular test object while the detection is carried out on the outside. Irrespective of the particular configuration of the test object, a running and continuous inspection program is preferably carried, and may be automated to a high degree and recorded. If certain empirically ascertained critical values in the detection pattern are exceeded, a certain alarm-like indication may be provided for in order to alert personnel that the tested object has in a particular location a defect. In addition, or in lieu thereof, there may be provided an automatically operated marking device for marking the object at the spot of a detected defect.

DESCRIPTION OF THE DRAWINGS

While the specification concludes with claims particularly pointing out and distinctly claiming the subject matter which is regarded as the invention, it is believed that the invention, the objects and features of the invention, and further objects, features and advantages thereof will be better understood from the following description taken in connection with the accompanying drawings in which:

Figure 1:
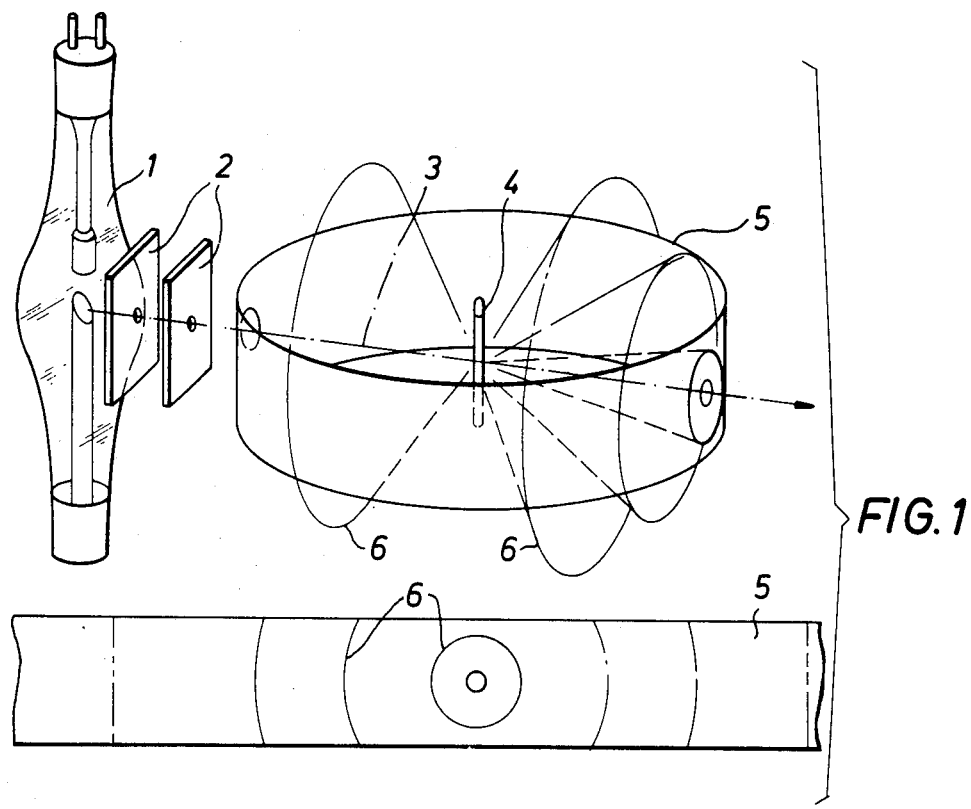
FIG. 1 is a somewhat schematic drawing illustrating in principle x-ray fine texture investigation, of unoriented crystallites.

Proceeding now to the detailed description of the drawings, FIG. 1 demonstrates the principle of x-ray fine texture under utilization of a powder sample, i.e., a sample of completely unoriented crystallites as test object. This test method has become known as the Debye-Scherrer method. In particular, an x-ray tube 1 emits an x-ray 3 passing through a set of diaphragms 2, and penetrating a object 4, being, for example, a compound object. Around the test object is provided a film, i.e., a photosensitive or, better, an x-ray sensitive film material 5 having an opening but responding to the diffraction pattern 6 as emanating from the test object 4. The lower portion of FIG. 1 illustrates the geometric development of the film 4, i.e., the ring 5 is projected into a plane, and the lines 6 herein represent the diffraction pattern as it will appear on the developed film.

The aforementioned method contrasts with the particular inventive method which is an x-ray fine texture wide angle method and uses test objects being composed of fibers embedded e.g. in resin. Herein crystallites, i.e., the above defined microparacrystallites, have a particular orientation in relation to a crystal axis running in the direction of extension of the fibers. This orientation is the same, or basically the same, for all fibers. Therefore, in this particular test case the x-ray 3 penetrates the fiber bundle of the test object and impinges upon the film portion 5 serving here as a wide angle detector. The film will image the reflections 7 and 8, which are the result of wide angle deflection and scatter of the x-ray 3 by the particular microparacrystallite structure of the individual fibers. The particular images 7 and 8 show, by way of example, that carbon fibers in the test object 4 are in fact oriented in the direction of the arrow 9. If one considers the physical properties of such test objects, for example, usual compound objects such as polypropylene, CFK, Kevlar, or the like, they do constitute a paracrystalline configuration oriented more or less accurately in the direction of the fibers (9). The x-rays are reflected on the lattice and crystal planes within each of these fibers.

Figure 2:
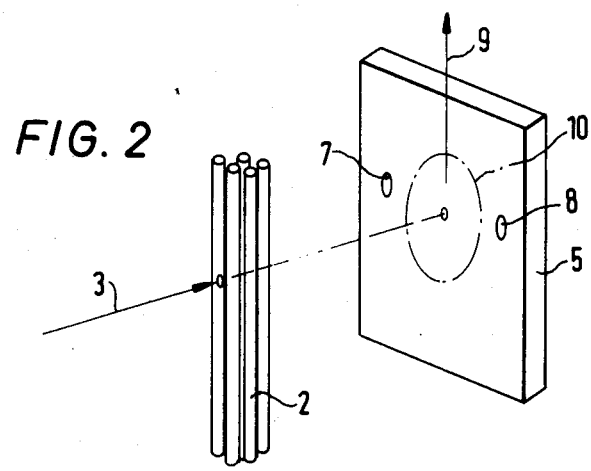
FIG. 2 is a schematic representation of an x-ray fine texture wide angle test under utilization of a fiber structure with oriented microparacrystallite configuration.

In the case of compound materials, including carbon fibers, the carbon atoms provide ordered chainlike molecular structure, and these in turn produce an ordered unambiguous pattern of reflection. On the other hand, any surrounding and embedding resin (host material) used as binder and filler establishes a more or less randomly distributed quantity of molecules which do not exhibit a preferred direction, particularly as far as interaction with x-rays is concerned, and therefore will result in annular reflection rings, such as 10 in FIG. 2. Therefore, one can readily see that the fine texture investigation used as here, and using particularyly monochromatic x-rays, result in distinguishing reflection and diffraction images for the fibers on one hand, and the filler and the binder material on the other hand.

Figure 3:
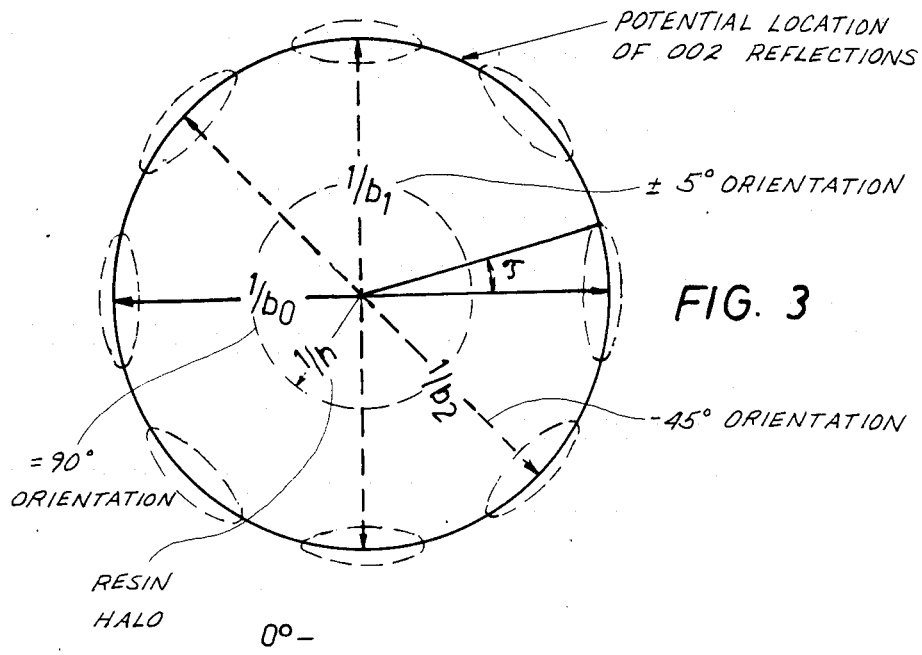
FIG. 3 depicts examples of possible reflexes resulting from a carbon fiber compound system.

As shown now is greater detail in FIG. 3, the reflection of a carbon fiber compound system may exhibit a more complex pattern. One can see here the particular so-called 002 reflection on carbon with different fibers and different angles within a more complex compound system, and one sees also a halo-like pattern which is produced by the resin in which the fibers are embedded.

The distance b between two adjacent graphite lattice planes 002 of a compound system have a direct geometric relation to the reflection distances from the zero point. In a first approximation such a distance is directly receiprocal to the distance b of the lattice planes, i.e., they are depicted in the x-ray image with a proportional factor of 1/b. FIG. 3 illustrates reflection with the index 0 in representation of fibers which are oriented perpendicular to the plane of the drawings. Reflections with index 1 represent 1/b1, which in turn represents fibers which are oriented perpendicularly to the formula. In these instances the disposition of the reflection may vary by plus or minus 5 degrees.

The reflection, i.e., index 2 corresponding to 1/b2, represent fiber orientation in the diagonal. $2\pi$ is the half width value of the reflection in the tangential direction, which in turn is an indication of the quality with regard to parallel orientation of the microparacrystals in the direction of the orientation of the fibers themselves, and depends on the texture of a fibril, i.e., of a single fiber, and further on the quality of the disposition of a strand. 1/h represents the halo that is indicative of the disposition of the resin without any orientation being indicated. It is thus possible to detect how the fibers are oriented in a compound part of structural material just through the disposition of the reflection. The tangential half width value which is half of the angle $\tau$ of the 1/b location of a reflection image is here particular a directly indicating parameter for the quality of the fibers, i.e., it is an indicator for the degree and extent of orientation of the respective fibers.

Upon investigating fiber reinforced compound paths by means of monochromatic x-rays, the following effects can be measured and certain inferences can be derived therefrom.

| MEASUREMENT | EFFECT CAUSED BY | INFERENCE ABOUT |
|---|---|---|
| Intensity of reflection | Number of lattice planes (microparacrystals) in the test beam (proportional) | Number of fibers per unit area (depends on type of fiber) |
| Angle of reflection in relation to an axis of symmetry of the test object | angle of lattice plane to fiber axis | disposition of fiber direction relative to axis of symmetry of test object (angle or looping) |
| Azimuthal width of reflection | Scatter of lattice planes | Orientation of the fibers |
| Radial distance of reflections from center | Distance of lattice planes | Type of material (fiber brand) internal stress, purity |
| Radial width of reflection | Paracrystalline defects and size of main paracrystals | Impurities, density of internal surfaces; mechanical stability |
| Halo of metallic coatings (e.g. AL) | Irregularly distributed lattice planes of vapor deposited crystals | Layer thickness and purity of protective layers |
| Halo of resin | Irregular distributed molecules | Purity of brand or type of fiber |

Figure 4:
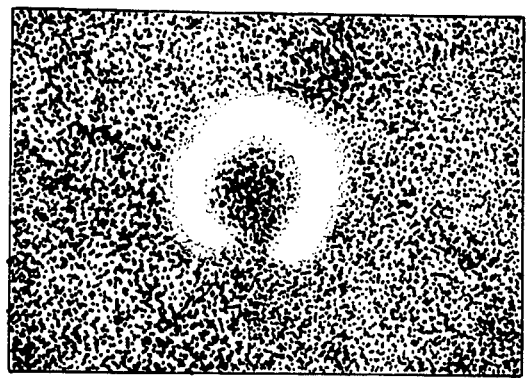

In the following it will be explained how by means of this matrix various inferences can be drawn with regard to the test object. For example, FIG. 4 illustrates a halo without further discernible structure. This image therefore can be interpreted as a resin system which does not include any fibers. Therefore, it can serve as a kind of reference for purpose of identifying the reflections resulting from interaction between resin and x-rays. The spot in the center of the halo, as well as the break in the halo, are actually produced by the lead diaphragm for extracting the primary x-ray.

Figure 5:
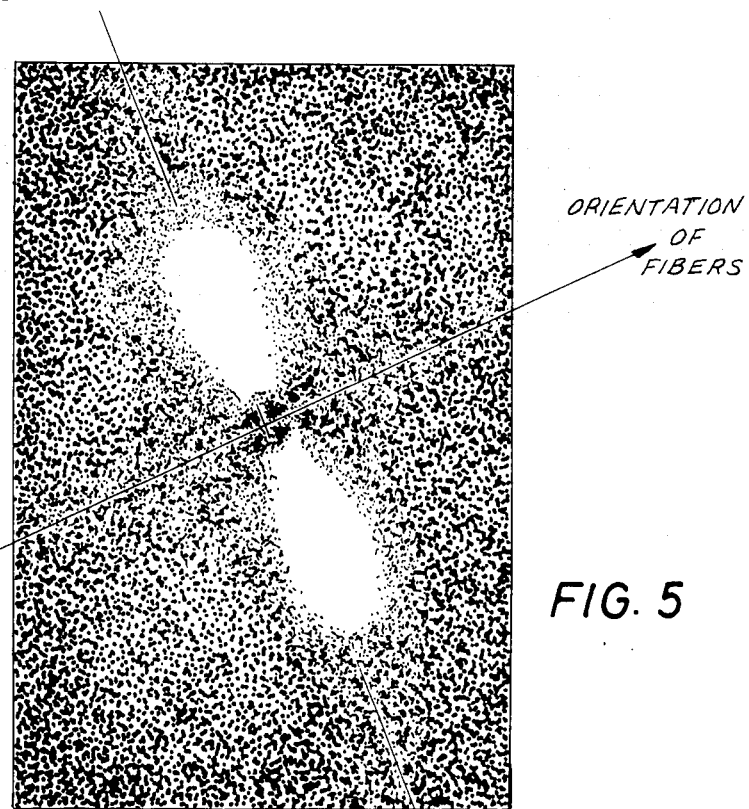
FIGS. 4, 5 and 6 are microcrystallite x-ray refraction and scatter pictures for different test objects to be described below.
Figure 6:
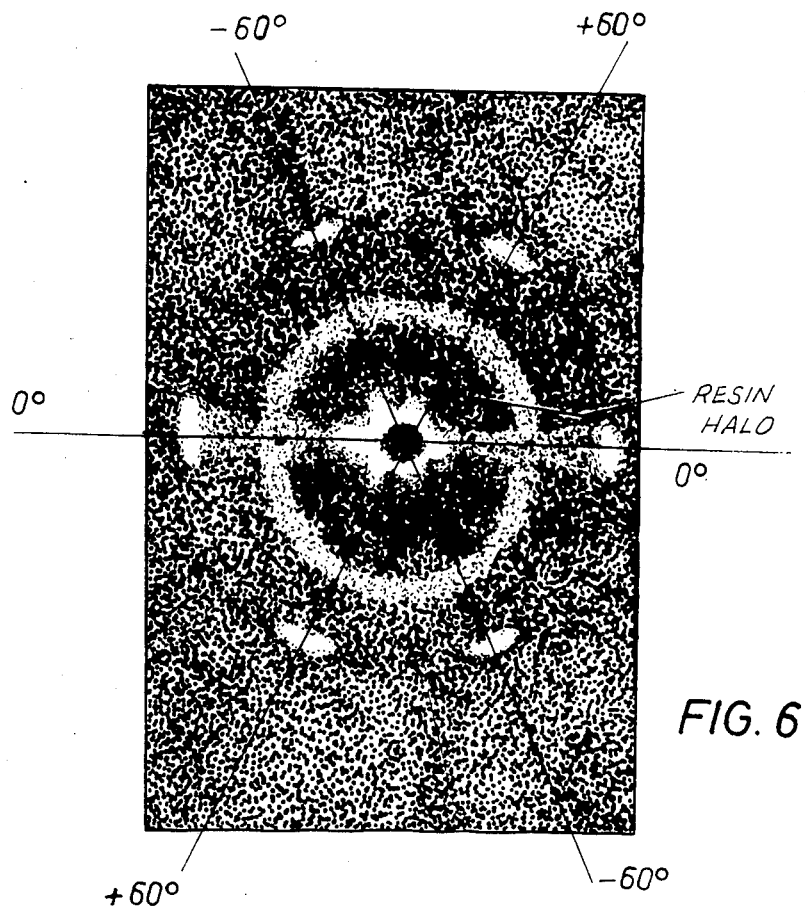

FIG. 5 illustrates the reflection of a fiber reinforced compound system in direct representation of the orientation of the fibers as can be extracted from these images. FIG. 6 shows also reflection of a fiber reinforced compound system with fibers included being oriented in several directions.

It can thus be seen that the x-ray method as explained here permits the non-destructive testing of fiber reinforced compound materials, and the test results can be unambiguously interpreted.

The x-ray source may have, for example, several windows through which x-ray beams emerge, whereby the windows for the primary rays and the reflexes may be configured in terms of different diaphragm contours, for example, triangularly, circularly, a star pattern, quadrilaterally, or the like. These diaphragm patterns should be matched to the pattern of the fibers in the compound object. An x-ray sensitive film can be used, as stated, and diaphragms can be used in conjunction therewith to create a particular response to particular reflections or reflective components. Alternatively, electronic detectors can be used, including, for example, scintillation counter, solid state detectors, or the like. These kind of detectors will be used particularly in those cases where there is a running and continuous testing of the object. These detectors then provide electrical outputs permitting correspondingly running registration and continuous data acquisition in a suitable manner. Special diaphragms can be used in conjunction therewith in order to obtain larger intensities, particularly in the direction of the fiber bundle, and they may be of slot-like orientation, the slot extending in the direction of the fiber to thereby increase the yield. The detectors may be provided with automation as far as positioning is concerned, for purposes of adjusting their position to points and locations of maximum reflected x-ray intensity. In an alternative version, test object and detector system can be moved in relation to each other, whereby, for example, the detector or film and the x-ray source are stationary and the object is continuously passed through the detector zone. In the case of a tubular object, the continuous motion may involve rotation about the longitudinal axix, for example, in order to ascertain uniform distribution of looped around compound fibers, and the uniformity involves cross section and number of fibers. Alternatively, but still for a tubular object, a helical and/or a meandering motion may be used to progressively pass different portions of the test object passed the stationary detector; the x-ray tube may be on one side, and the detector on the other side. However, if a rod-like x-ray tube is used, this tube may be the interior of the hollow or tubular object.

Particularly in the case of a continuous measuring program with progressively passing different portions of the test object through the detection and inspection zone, one may simultaneously measure several, i.e., at least two reflection in different locations in a measuring plane, and to provide for an electronic differential circuit that compares the x-ray intensities of the two reflections. For example, in the case of a carbon fiber as stated, two basic reflections on the so-called 002 crystal lattice plane can be separately detected under utilization of separate diaphragms, and the outputs are compared. For example, there may be a width difference in the reflection parallel to the extension of the fiber, and that width difference of the two reflections may be indicative of the quality with regard to the orientation of the microparacrystals inside of the fiber strands. One should in this case use diaphragms of differently wide aperture. Two reflections ascertained separately and processed in a differential circuit constitute information with regard to the constancy of fiber thickness and strength based on the mass of the microparacrystals per cross section. Aside from evaluating the strength orientation and quality as far as fiber distribution is concerned, it is also possible to ascertain the relative portion of the randomly distributed molecules of the binder or filler. This requires adjustment of the equipment to ascertain the respective halo which is set up by the randomly distributed crystals, and the evaluation may be photometrically established. This then becomes an indicator for the quality of the binder such as a resin.

The examples above have centered on the testing of fiber reinforced products. However, the method is applicable in all cases of compound materials, in which the different components yield different x-ray diffraction and reflection patterns. This is the case for instance in vehicle tires such as carcasses.

The invention is not limited to the embodiments described above, but all changes and modifications thereof, not constituting departures from the spirit and scope of the invention are intended to be included.

What is claimed is:

1. Method for non-destructive testing of fiber reinforced structural materials under utilization of x-rays and detection comprising the steps of:

irradiating a sample or sample portion of the compound part with monochromatic x-rays; and detecting disposition and configuration of diffracted and refracted x-ray patterns on account of interaction with polycrystal material in the interior wherein different patterns result from differences in crystaline structure of the fibers and the host material in order to determine details and particulars of the fibers in said object.

2. Method as in claim 1 and including the step for continuously moving the object and the detector in relation to each other.

3. Method as in claim 1, said object being of tubular configuration, said object rotating continuously about its longitudinal axis.

4. Method as in claim 1, said object being of tubular configuration, said object being moved in relation to the detector in a helical fashion.

5. Method as in claim 1, said object being of tubular configuration and using the step of generating the x-ray in the interior of said tubular object, and detecting said reflection on the outside.

6. Method as in claim 1 and including the step of separately detecting two different reflections; providing electrical signals representative thereof; and ascertaining an indication of difference between said signal on a running basis.

7. Method as in claim 6 wherein said two different reflections pertain to reflections on particular planes, and using two diaphragms with different apertures and obtaining said difference corresponding thereto.

8. Method as in claim 1 including the step of separately detecting a reflective halo resulting from reflection on randomly distributed filler material in said object, and on separately detecting particular reflection resulting from crystal orientation in fibers embedded by said binder.

9. Method as in claim 1 and including the step of localizing the detection in particular orientation to the test object and the primary x-ray.

10. The method as in claim 1 including using a diaphragm that has a slot in direction of the fiber.

11. The method as in claim 9 including the step of positioning the detector to maximize output.

12. Method as in claim 1 and including the step of measuring the width of a reflection.

13. Method as in claim 1 and including the step of ascertaining deviation from a selected standard.

14. Method as in claim 13 and including the step of marking the location of a detected defect.

15. Method as in claim 1 said object being of tubular configuration, said object being moved in a relation to the detector in a meandering fashion.

* * * * *